United States Patent [19]

Erikson

[11] 4,117,836
[45] Oct. 3, 1978

[54] CATHETER FOR SELECTIVE CORONARY ARTERIOGRAPHY OF THE LEFT CORONARY ARTERY

[75] Inventor: Uno Eugeń Erikson, Uppsala, Sweden

[73] Assignee: Siemens-Elema AB, Solna, Sweden

[21] Appl. No.: 698,997

[22] Filed: Jun. 23, 1976

[30] Foreign Application Priority Data

Jun. 23, 1975 [SE] Sweden .................................. 7507201

[51] Int. Cl.² ............................................. A61M 25/00
[52] U.S. Cl. ................................ 128/2.05 R; 128/348; 128/DIG. 9
[58] Field of Search ................. 128/2 A, 2 M, 2.05 R, 128/348–351, DIG. 9

[56] References Cited

FOREIGN PATENT DOCUMENTS 930,636   7/1973   Canada ..................................... 128/348
7,214,253 5/1974   Sweden .................................... 128/348

OTHER PUBLICATIONS

Cordis Phamphlet, "Cordis Ducor" pp. 2, 8, 1973.
U.S.C.I. Phamphlet, "Bourassa Cardiovascular Catheters" Jun. 1972.
Bourassa et al., "Amer. Jour. Roentgenology, Rad. Ther. & Nuclear Med." vol. CVII, No. 2, 1964.

Primary Examiner—Dalton L. Truluck
Attorney, Agent, or Firm—Fred Philpitt

[57] ABSTRACT

A catheter for selective coronary arteriography of the left coronary artery, which catheter comprises a main part and an end section which latter comprises by turn from the main part a slightly curved part, a first short strongly curved part, a straight part, a second short strongly curved part and a short end part which is shaped to end in a taper and which catheter is provided with a perforation in the second strongly curved part or just before the beginning thereof and on the side of the catheter which is facing the onlooker when the catheter is placed with the curvatures clockwise from the main part.

4 Claims, 3 Drawing Figures

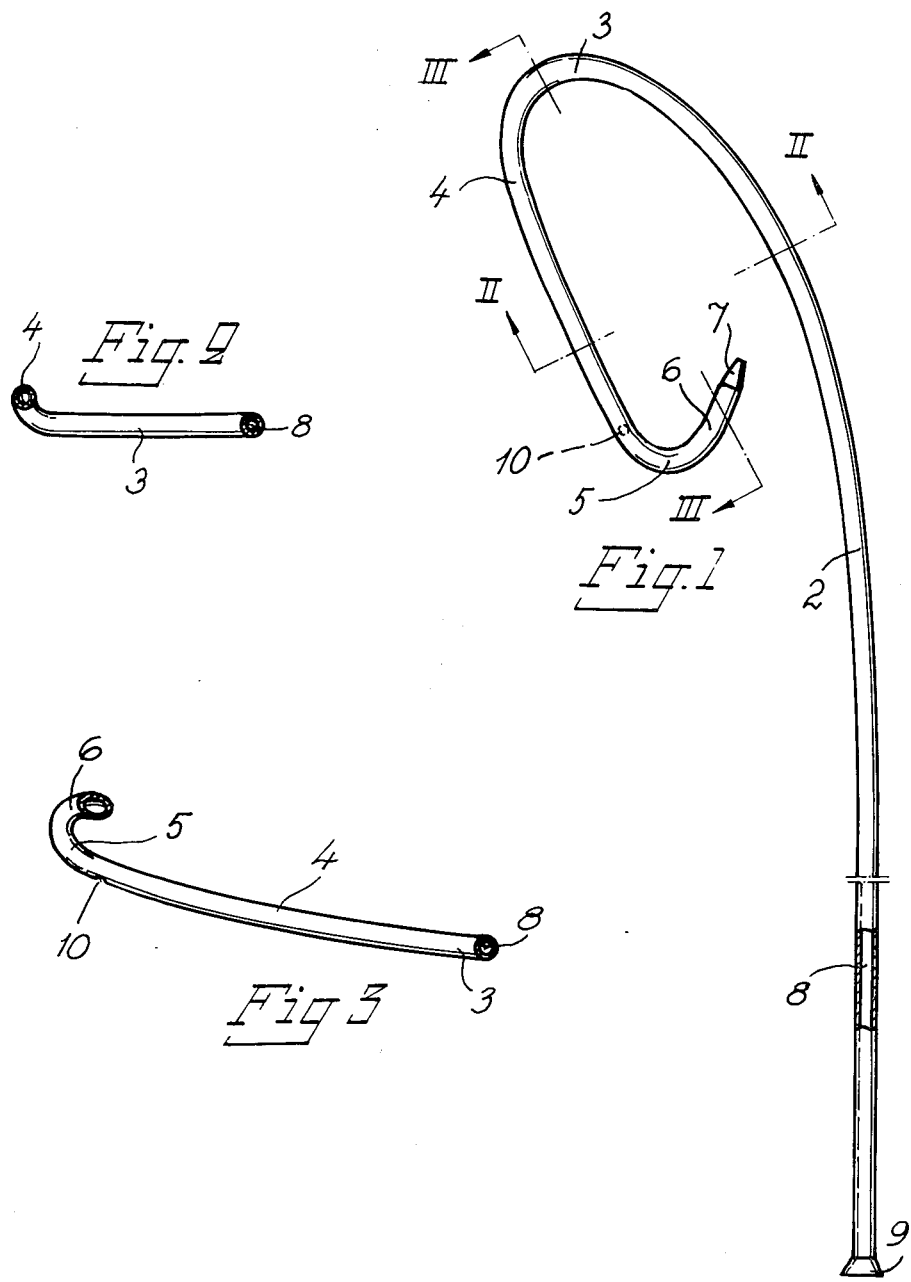

CATHETER FOR SELECTIVE CORONARY ARTERIOGRAPHY OF THE LEFT CORONARY ARTERY

The present invention relates to a catheter for selective coronar arteriography of the left coronary artery which catheter comprises a main part and an end section which latter comprises by turn from the main part a slightly curved part, a first short strongly curved part, a straight part, a second short strongly curved part and a short end part which is shaped to end in a taper.

Such a catheter is previously disclosed in Radiology, 89 (1967), 815–827. The insertion of this known catheter into the left coronary artery often meets with trouble in that the end of the catheter slips down into the non-coronary sinus instead of the artery or that the end runs against the wall of the artery so that the opening of the catheter is blocked, thus obstructing aspiration through the catheter. On attempts to set the tapered end free the catheter will easily slip out from the artery.

According to the present invention a catheter of the above mentioned type for selective coronary arteriography of the left coronary artery is provided, which catheter always can aspire and in addition affords the advantages of giving contrast filling also of coronary sinus so that the artery departure is also filled and in a preferred embodiment it will be easier to obviate the introduction of the tapered end into non-coronary sinus.

The catheter according to the invention is characterized by being provided with a perforation in the second strongly curved part or just before the beginning thereof and on the side of the catheter which is facing the onlooker when the catheter is placed with the curvatures clockwise from the main part.

According to a preferred embodiment the straight part and the second strongly curved part and the end part are inclined from the level of the main part of the catheter when the catheter is placed with the curvatures counter-clockwise from the main part. According to a particularly preferred embodiment the inclination of the second strongly curved portion is stronger than the inclination of the straight part. The total inclination to the tapered end of the catheter in the last mentioned case may be about 15 mm, the inclination of the straight part being about 5 mm thereof.

The invention will be further described in the following with reference to the enclosed drawing wherein FIG. 1 shows an enlarged side view partly in section of an embodiment of the catheter according to the invention, FIG. 2 shows section II—II in FIG. 1 and FIG. 3 shows section III—III in FIG. 1.

The catheter shown in the figures comprises a main part 1 and an end section which latter comprises a slightly curved part 2, a first strongly curved part 3, a straight part 4, a second short, strongly curved part 5 and a short end part 6 which is shaped to end in a taper 7. The catheter is further provided with a channel 8 throughout the catheter and a connection flange 9 arranged at the free end of the main part. A perforation 10 is provided in the second strongly curved part 5 in the side wall of the catheter which in FIG. 1 is turned away from the onlooker. This perforation 10 connects the channel 8 with the surroundings outside the catheter and enables blood to penetrate into the channel 8 independent of whether the taper 7 is blocked or not by resting against the wall of the artery. Furthermore, on injection of a contrast agent through the catheter, part of the contrast agent will pass through the perforation 10 into the coronary sinus thus enabling the visualization thereof.

As is seen in FIGS. 2 and 3 the straight part 4, the second strongly curved part 5 and the end part 6 are inclined from the level of the main part of the catheter, the inclination of the curved part 5 and the end part 6 being considerably stronger than the inclination of the straight part 4. The slightly curved part 2 and the first strongly curved part 3 are at the same level as the main part.

According to the figures, the perforation is located at the beginning of the strongly curved part 5. The preferred location of the perforation is in a zone from 1 to 2 mm before the beginning of the second strongly curved part to 1 to 2 mm after the middle of said part.

What is claimed is:

1. A catheter for selective coronary arteriography of the left coronary artery, which catheter comprises an elongated, tubular member having an interior channel therein extending the length of said catheter, said catheter having a main part and an end section which latter comprises by turn from the main part a slightly curved part, a first short strongly curved part, a straight part, a second short strongly curved part and a short end part which is shaped to end in a taper, which catheter is characterized by being provided with a single perforation just means opening into the tubular channel in said straight part at the end thereof before the beginning of the second strongly curved part and on the side of the catheter which is facing the onlooker when the catheter is placed with the curvatures clockwise from the main part.

2. A catheter according to claim 1, wherein said straight part, said second strongly curved part and said end part are inclined from the level of said main part of the catheter when the catheter is placed with the curvatures counter-clockwise.

3. A catheter according to claim 2, wherein the inclination of said second strongly curved part is stronger than the inclination of said straight part.

4. A catheter according to claim 3, wherein the total inclination to the end of said taper is about 15 mm, the inclination of the straight part being about 5 mm thereof.

* * * * *